United States Patent
Williams et al.

(10) Patent No.: US 10,709,378 B2
(45) Date of Patent: Jul. 14, 2020

(54) CLOSED LOOP NEURAL ACTIVITY TRIGGERED REHABILITATION DEVICE AND METHOD

(71) Applicant: Wisconsin Alumni Research Foundation, Madison, WI (US)

(72) Inventors: Justin C. Williams, Cambridge, WI (US); Vivek Prabhakaran, Fitchburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 198 days.

(21) Appl. No.: 15/289,662

(22) Filed: Oct. 10, 2016

(65) Prior Publication Data

US 2017/0020448 A1     Jan. 26, 2017

Related U.S. Application Data

(63) Continuation of application No. 12/715,090, filed on Mar. 1, 2010, now abandoned.

(51) Int. Cl.

| | |
|---|---|
| *A61B 5/04* | (2006.01) |
| *A61N 1/36* | (2006.01) |
| *A61B 5/00* | (2006.01) |
| *A61B 5/0482* | (2006.01) |
| *A61B 5/0476* | (2006.01) |

(52) U.S. Cl.
CPC .......... *A61B 5/4836* (2013.01); *A61B 5/0476* (2013.01); *A61B 5/0482* (2013.01); *A61N 1/36003* (2013.01); *A61N 1/36014* (2013.01); *A61B 2505/09* (2013.01)

(58) Field of Classification Search
None
See application file for complete search history.

(56) References Cited

U.S. PATENT DOCUMENTS

| | | | |
|---|---|---|---|
| 6,171,239 B1 * | 1/2001 | Humphrey | ........... A61B 5/0482 600/372 |
| 6,175,762 B1 * | 1/2001 | Kirkup | ................. A61B 5/0482 600/544 |
| 7,231,254 B2 | 6/2007 | DiLorenzo | |
| 2003/0074032 A1 | 4/2003 | Bradford | |
| 2006/0004422 A1 | 1/2006 | Dirk | |

(Continued)

OTHER PUBLICATIONS

Cramer et al., "Use of Functional MRI to Guide Decisions in a Clincial Stroke Trial", Stroke Journal of the American Heart Association, Apr. 14, 20015.

(Continued)

*Primary Examiner* — Etsub D Berhanu
(74) *Attorney, Agent, or Firm* — Boyle Fredrickson, S.C.

(57) ABSTRACT

A closed loop, neural activity triggered rehabilitation device and method are provided for facilitating recovery of a patient from the effects of a sensory motor disability. The device includes a sensor system positionable adjacent the brain of the patient. The sensor system detects neural signals. A functional stimulation component is operatively connectable to at least one body part, such as a muscle or a nerve. The functional stimulation component stimulates the at least one body part in response to the neural signals detected. A sensory stimulation module is operatively connected to the patient to provide sensory feedback thereto.

17 Claims, 3 Drawing Sheets

(56) References Cited

U.S. PATENT DOCUMENTS

| 2006/0167371 | A1* | 7/2006 | Flaherty | A61F 2/50 600/545 |
|---|---|---|---|---|
| 2007/0032738 | A1 | 2/2007 | Flaherty et al. | |
| 2007/0142864 | A1 | 6/2007 | Imad et al. | |
| 2008/0319505 | A1 | 12/2008 | Boyden et al. | |
| 2009/0306531 | A1 | 12/2009 | Leuthardt et al. | |

OTHER PUBLICATIONS

Jackson et al., "Empathy examined throught he neural nechanisms involved in imaging how I feel versus how you feel pain", Neuropsychologia 44 (2006) 752-761.

Knutson et al., "A Novel Functional Electrical Stimulation Treatment for Recovery of Hand Function in Hemiplegia: 12-Week Pilot Study", Neurorehabilitation and Nural Repair, Sep. 23, 2008.

Tyler et al., "Closing an Open-Loop Control System: Vestibular Substitution Through the Tonuge", Journal of Integrative Neuroscience, vol. 2, No. 2 (2003), 159-164.

Wilson et al., "ECoG Factors Underlying Multimodal Control of a Brain-Computer Interface", IEEE Transactions on Neural Systems and Rehabilitation Engineering, vol. 14, No. 2, Jun. 2006, p. 246.

Wilson et al., "Electrotactile vision-substitution matches vision-only performance in a brain-computer interface movement task", Neuroscience 2008, Nov. 19, 2008.

U.S. Appl. No. 12/715,090, Patent Trial and Appeal Board Decision, dated Aug. 9, 2016, 7 pages.

* cited by examiner

CLOSED LOOP NEURAL ACTIVITY TRIGGERED REHABILITATION DEVICE AND METHOD

CROSS-REFERENCE TO RELATED APPLICATION

This application is a continuation of U.S. application Ser. No. 12/715,090, filed Mar. 1, 2010.

REFERENCE TO GOVERNMENT GRANT

This invention was made with government support under RR25012, awarded by the National Institutes of Health. The government has certain rights in this invention.

FIELD OF THE INVENTION

This invention relates generally to brain injuries, and in particular, to a closed loop, neural activity triggered rehabilitation device and method that facilitates the recovery of a patient from the effects of a sensory motor disability.

BACKGROUND AND SUMMARY OF THE INVENTION

Injuries to the brain from trauma, stroke or the like are unfortunately, quite common. By way of example, each year, approximately 780,000 people suffer a new or recurrent stroke in the United States. Approximately 85% of these patients survive and require rehabilitation. As a result, stroke is the leading cause of long-term disability in the U.S. Nearly four million Americans are living with the effects of stroke, with millions of family and friends acting as caregivers, and the estimated direct and indirect costs of stroke continue to escalate. It is estimated that the cost of stroke between 2005-2050 will approach $2.2 trillion and the majority of these costs with be directed towards long-term care and rehabilitation.

As previously noted, the most common treatment for stroke is physical rehabilitation. It is well known in stroke rehabilitation that passive movement repetition from the afflicted limb can produce notable recovery of lost function. This process is traditionally done by physical therapists, who are limited by the number of repetitions that they can reasonably provide in one session. Physical therapists are also limited in the number of patients that can be seen for therapy during a given time period. This, in turn, may cause an undue burden on the rehabilitation clinic and potential lapses in the treatment regimen for potential patients.

While passive movement repetition can be an effective rehabilitation strategy, the recovery can be slow, painstaking and suboptimal. To circumvent this issue, several products have attempted to provide more automated methods to promote rehabilitation, although they have generally been hampered by cost (Robotic therapies) or effectiveness/invasiveness (implantable cortical stimulators). There is growing scientific evidence that points to closed-loop functional neural stimulation as a viable means of driving plasticity in both the intact and damaged nervous system.

Therefore, it is a primary object and feature of the present invention to provide a closed loop, neural activity triggered rehabilitation device and method that facilitates the recovery of a patient from the effects of a sensory motor disability.

It is a further object and feature of the present invention to provide a closed loop, neural activity triggered rehabilitation device and method that utilizes passive movement repetition of an afflicted limb with limited time requirements placed upon a physical therapist working with a patient.

It is a still further object and feature of the present invention to provide a closed loop, neural activity triggered rehabilitation device and method that is simple to implement and easy to use.

In accordance with the present invention, a closed loop, neural activity triggered rehabilitation device is provided for facilitating recovery of a patient from the effects of a sensory motor disability. The patient includes a brain and at least one body part. The device includes a sensor system positionable adjacent the brain. The sensor system detects neural signals. A functional stimulation component is operatively connectable to at least one body part, such as a muscle or a nerve. The functional stimulation component stimulates the at least one body part in response to the neural signals detected.

The device may further include a sensory stimulation module operatively connected to the patient to provide sensory feedback thereto. The sensory stimulation module includes a tongue stimulator operatively connectable to a tongue of the patient. A central processing unit interconnects the sensor system and the functional stimulation component. The central processing unit causes the functional stimulation component to stimulate the at least one body part in response to the neural signals detected. The sensor system includes an electroencephalography sensor.

It is contemplated for the at least one body part to be at one muscle and for the sensor system to include a plurality of sensors. It is also contemplated for the functional stimulation component to include a plurality of muscle stimulators connectable to the at least one muscle. The device may also include a central processing unit operatively connected to the plurality of muscle stimulators and a multichannel amplifier interconnecting each of the plurality of sensors to the central processing unit.

A sensory stimulation module operatively connected to the central processing unit and to the patient to provide sensory feedback thereto. The sensory stimulation module includes a tongue stimulator operatively connectable to a tongue of the patient. The functional stimulation component stimulates the at least one muscle in response to predetermined parameters including a location of the sensory motor disability and a time period since the one onset sensory motor disability.

In accordance with a further aspect of the present invention, a closed loop, neural activity triggered rehabilitation device is provided for facilitating recovery of a patient from the effects of a sensory motor disability. The patient includes a brain and a muscle. The device includes a plurality of sensors positionable adjacent the brain for detecting neural signals. A plurality of muscle stimulators are operatively connectable to the at least one muscle. The plurality of muscle stimulators stimulate the at least one muscle in response to the neural signals detected.

A sensory stimulation module is operatively connected to the patient to provide sensory feedback thereto. The sensory stimulation module includes a tongue stimulator operatively connectable to a tongue of the patient. A central processing unit interconnects the plurality of sensors and the plurality of stimulators. The central processing unit causes the plurality of stimulators to stimulate the at least one body part in response to the neural signals detected. The plurality of sensors are electroencephalography sensors.

The device may include a central processing unit operatively connected to the plurality of stimulators and a multichannel amplifier interconnecting each of the plurality of sensors to the central processing unit. In such arrangement, a sensory stimulation module may be operatively connected to the central processing unit and to the patient to provide sensory feedback thereto. The sensory stimulation module includes a tongue stimulator operatively connectable to a tongue of the patient.

In accordance with a still further aspect of the present invention, a method is provided for facilitating the recovery of a patient from the effects of a sensory motor disability. The method includes the step of measuring neural signals from a brain using scalp-electroencephalography waves. Electrical stimulation is provided to a body part (e.g. a muscle or a nerve) in response to the measured neural signals.

General sensory stimulation is applied to the patient in conjunction with the electrical stimulation. The general sensory stimulation may be applied to a tongue of the patient. In addition, the scalp electrodes may be positioned on the patient to measure the neural signals. It is contemplated for the scalp electrodes to be electroencephalography sensors. A function magnetic resonance imaging test may be conducted to determine a proper position of the scalp electrodes to measure the neural signals.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings.

DETAILED DESCRIPTION OF THE DRAWINGS

Figure 1:
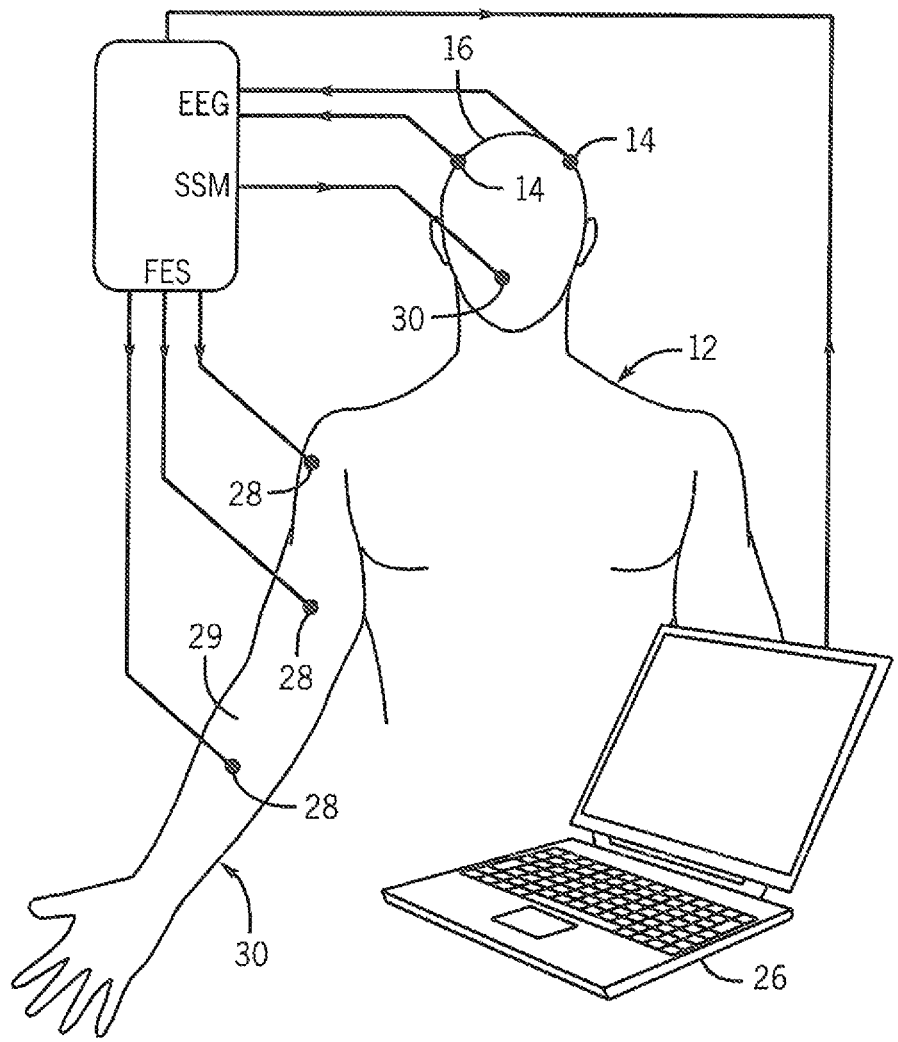
FIG. 1 is a first schematic view of a rehabilitation device in accordance with the present invention interconnected to a patient.
Figure 2:
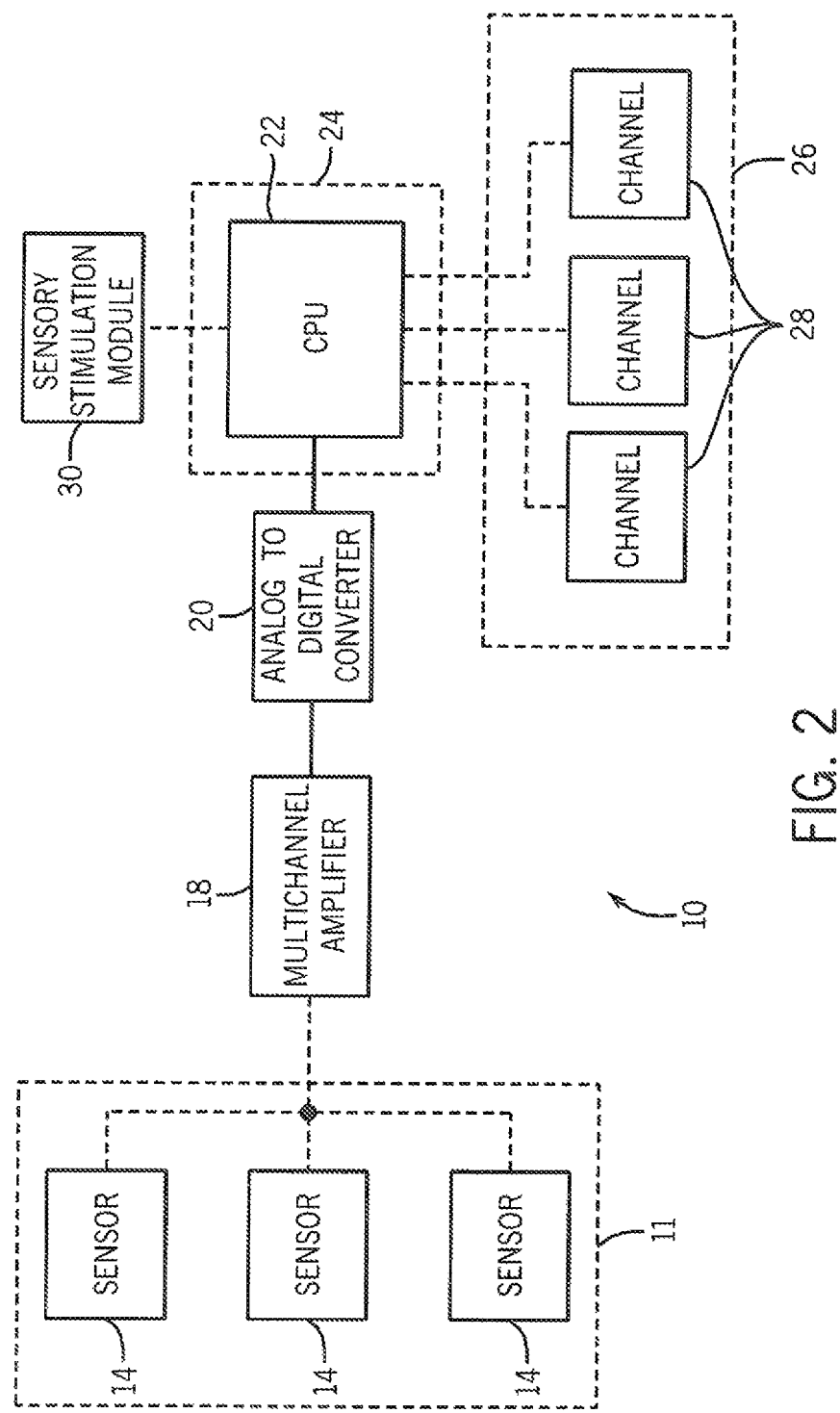
FIG. 2 is a second schematic view of a rehabilitation device in accordance with the present invention.

Referring to FIGS. 1-2, a closed loop, neural activity triggered rehabilitation device in accordance with the present invention is generally designated by the reference numeral 10. It is intend for rehabilitation device 10 to facilitate the recovery of patient 12 from the effects of a sensory motor disability, e.g. from a stroke, as hereinafter described. Rehabilitation device 10 includes sensor system 11 having an array of electroencephalography sensors 14 positionable on scalp 16 of patient 12 to measure fluctuations in electrical potential associated with real-time volitional command signals from the motor cortex. As is known, the motor cortex is the area of the cerebral cortex wherein impulses from the nerve centers to the muscles originate. The neural activity detected by the plurality of electroencephalography sensors 14 corresponds to a spacio-temporal sequence of neural activity in the immediate vicinity of sensors 14. It has been found that by determining the spatiotemporal patterns of neural activity detected by array of electroencephalography sensors 14, one may determine the volitional command signal from the motor cortex uniquely associated therewith. Hence, these spatiotemporal patterns can be correlated to a patient's desire to move a specific muscle in the patient's arm or leg.

The array of electroencephalography sensors 14 are operatively connected to a multichannel electroencephalography amplifier 18 which, in turn, is operatively connected to analog-to-digital converter 20. Analog-to-digital converter 20 is connected to a central processing unit (CPU) 22 of a conventional computer, such as laptop computer 24 through a USB connector or the like. It is intended for CPU 22 to execute a control system algorithm stored on laptop computer 24, as hereinafter described, to effectuate the methodology of the present invention.

Rehabilitation device 10 further includes a multichannel functional electric stimulation (FES) component 26 operatively connected to CPU 22 of laptop 24 through a USB connection or the like. It is intended for each channel 28 of FES component 26 to be operatively connected to at least one body part, such as muscle 29, of patient 12 to activate the body part. By way of example, each channel 28 of FES component 26 may include a pair of surface electrodes engageable with the skin of patient 12 for nerve stimulation of the underlying tissue. More specifically, CPU 22 provides controlled current pulses to the pairs of surface electrodes of each channel 28 of FES component 26 which, in turn, are applied to the skin of patient 12. By providing controlled electrical pulses to each channel 28 of FES component 26, unique, synchronized current pulses may be applied at different muscle sites thereby stimulating coordinated limb movement.

Rehabilitation device 10 also includes sensory stimulation module 30 operatively connected to CPU 22 of laptop 24 through a USB connection or the like. It is intended for sensory stimulation module (SSM) 30 to provide sensory feedback to patient 12 and to increase the general excitability of the afflicted sensory-motor system of patient 12 through latent intact neural pathways. Bach-y-rita, U.S. Pat. No. 6,430,450, entitled "Tongue Placed Tactile Output Device," discloses an exemplary sensory stimulation module for use in conjunction with the rehabilitation device of the present invention. The Bach-y-rita '450 patent is assigned to the assignee of the present invention and is incorporated by reference into the present application as if fully described herein. The tongue placed, tactile output device disclosed in the '450 patent includes an array of tactile elements integral with a mouth part sized to be received and stabilized within the mouth. The array of tactile elements is positioned over a lower surface of the mouth part so as to be in contact with the tongue when the mouth part is received within the mouth. In response to the control system algorithm, CPU 22 provides spatially encoded signals to the array of tactile elements to selectively excite selected ones of the array of tactile elements, for reasons hereinafter described.

In order to effectuate the methodology of the present invention, patient 12 undergoes a functional magnetic resonance imaging (fMRI) test to determine a proper position of array of electroencephalography sensors 14 on scalp 16 to measure fluctuations in electrical potential associated with real-time volitional command signals from the motor cortex of patient 12. As is known, an (fMRI) test allows one to identify which areas of a sensory motor disability victim's motor cortex are being used by patient 12 in an attempt to move at least one selected muscle 29 in limb 30 of patient 12.

Once the areas of a victim's motor cortex are identified, array of electroencephalography sensors 14 are positioned on scalp 16 of patient 12 at the located areas to measure fluctuations in electrical potential associated with real-time volitional command signals from the motor cortex of patient 12. The mouth part of sensory stimulation module 30 is inserted into the mouth of patient 12 such that the array of tactile elements of sensory stimulation module 30 is positioned over a lower surface of the mouth part so as to be in contact with the tongue of patient 12. In addition, each channel 28 of FES component 26 is operatively connected to at least one muscle 29 of patient 12 to contract the at least one selected muscle 29 in selected limb 30 of patient 12.

In operation, the fluctuations in electrical potential associated with real-time volitional command signals from the motor cortex detected by array of electroencephalography sensors 14 are amplified by multi-channel amplifier 18 and converted into digital data by an analog to digital converter 20. The digital data is provided to CPU 22 which, in response to the digital data and the control system algorithm, generates spatially encoded signals for transmission to sensory stimulation module 30 and controlled current pulses for transmission to each channel 28 of FES component 26. It is contemplated for the control system algorithm executed by CPU 22 to be dependent on a physician selected set of parameters based upon the individual needs of patient 12. By way of example, these parameters may include the location of a stroke in patient 12, the motor deficits suffered by patient 12 as a result of the stroke, the time passed since the stroke, and/or the like). It is intended for a physician to use laptop 24 to input the selected set of parameters into the control system algorithm.

As heretofore described, the unique, synchronized current pulses supplied by CPU 22 to each channel 28 of FES component 26, stimulates contraction of the selected at least one muscle 29 of limb 30. In addition, the spatially encoded signals transmitted by CPU 22 to the array of tactile elements of sensory stimulation module 30 selectively excite selected tactile elements of the array of tactile elements. By selectively exciting selected tactile elements, sensory feedback is provided to patient 12 so as to increase the general excitability of the afflicted sensory-motor system of patient 12 through the patient's latent intact neural pathways.

Figure 3:
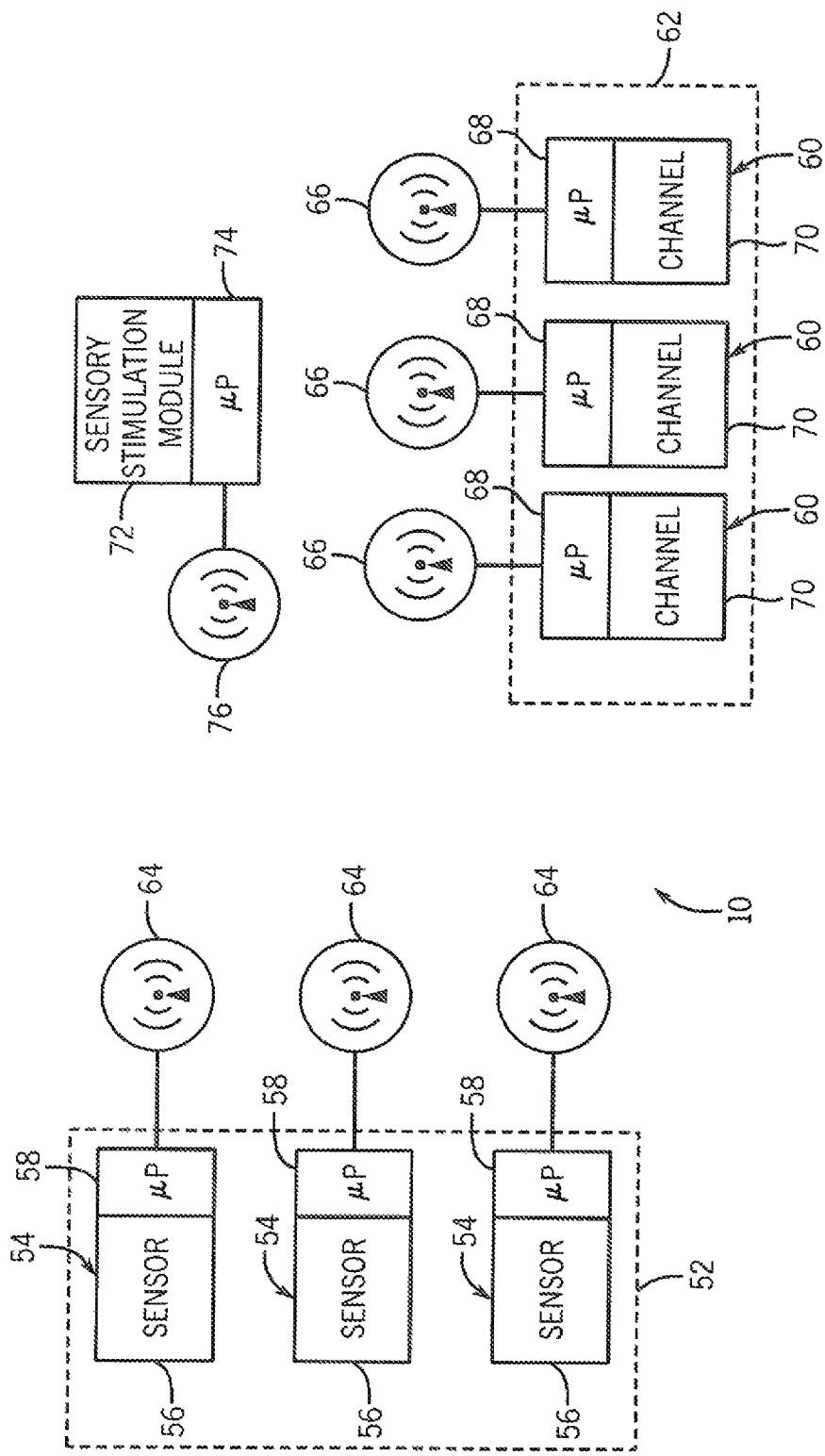
FIG. 3 is a schematic view of an alternate embodiment of a rehabilitation device in accordance with the present invention

Referring to FIG. 3, an alternate embodiment of a closed loop, neural activity triggered rehabilitation device in accordance with the present invention is generally designated by the reference numeral 50. It is intend for rehabilitation device 50 to facilitate the recovery of patient 12 from the effects of a sensory motor disability, e.g. from a stroke, as hereinafter described. Rehabilitation device 50 includes sensor system 52 having an array of electroencephalography sensor modules 54. Each sensor module 54 includes electroencephalography sensor 56 positionable on scalp 16 of patient 12 to measure fluctuations in electrical potential associated with real-time volitional command signals from the motor cortex, for reasons heretofore described. The neural activity detected by each sensor 56 corresponds to a temporal sequence of action potentials of the neurons in the immediate vicinity thereof.

Sensor modules 54 also include microprocessors 58 for receiving digital data from sensors 56 that corresponds to fluctuations in electrical potential associated with real-time volitional command signals from the motor cortex detected. Microprocessors 58 of sensor modules 54 may communicate with each other and generate spatially encoded signals for transmission to functional electric stimulation modules 60 of stimulation system 62 via wireless communicators 64. Functional electric stimulation modules 60 are operatively connected to wireless communicators 66 for receiving the spatially encoded signals transmitted to functional electric stimulation modules 60 by sensor modules 54 and for supplying the same to microprocessors 68 of functional electric stimulation modules 60. It is intended for channels 70 of functional electric stimulation modules 60 to be operatively connected to microprocessors 68 and to at least one body part, such as muscle 29, of patient 12, to activate the body part. By way of example, each channel 70 may include a pair of surface electrodes engageable with the skin of patient 12 for nerve stimulation of the underlying tissue. In response to the spatially encoded signals received, microprocessors 68 provide controlled current pulses to the pairs of surface electrodes of channel 70 which, in turn, are applied to the skin of patient 12. By providing controlled current pulses to channel 70, unique, synchronized current pulses may be applied at different muscle sites thereby stimulating coordinated limb movement.

It is further contemplated to insert sensory stimulation module 72 into the mouth of patient 12 such that the array of tactile elements of sensory stimulation module 72 is positioned over a lower surface of the mouth part so as to be in contact with the tongue of patient 12. Sensory stimulation module 72 is operatively connected to microprocessor 74 which, in turn, is operatively connected to wireless communicator 76. Wireless communicator 76 is adapted for receiving spatially encoded signals transmitted by sensor modules 54 and/or by functional electric stimulation modules 60. In response to the spatially encoded signals received, microprocessor 74 selectively excites selected tactile elements of the array of tactile elements of sensory stimulation module 72. By selectively exciting selected tactile elements, sensory feedback is provided to patient 12 so as to increase the general excitability of the afflicted sensory-motor system of patient 12 through the patient's latent intact neural pathways.

Various modes of carrying out the invention are contemplated as being within the scope of the following claims particularly pointing out and distinctly claiming the subject matter which is regarded as the invention.

We claim:

1. A closed loop, neural activity triggered rehabilitation device for facilitating recovery of a patient from the effects of a sensory motor disability, the patient including a brain and at least one muscle, the device comprising:

a sensor system positionable adjacent the brain at a predetermined location, the sensor system configured to detect real-time neural signals at the predetermined location corresponding to an area of the brain used by the patient to move a limb having plurality of muscle sites contemporaneously with volitional commands of the brain by the patient;

a control system operatively connected to the sensor system for receiving the real-time neural signals from the sensor system, the control system generating a plurality of unique, synchronized control signals which are based solely on the real-time neural signals detected by the sensor system and a predetermined set of patient parameters, without utilizing any neural signals of the patient obtained previous to and non-contemporaneously with the real-time neural signals, wherein the predetermined set of patient parameters is entirely independent of real time patient feedback; and a functional stimulation component operatively connectable to the control system and including a plurality of channels, each channel of the plurality of channels operatively connectable to a different muscle site of the limb and being adapted to receive a corresponding one of the plurality of unique, synchronized control signals and to stimulate a corresponding different muscle site in response to the corresponding one of the plurality of unique, synchronized control signals received from the control system.

2. The device of claim 1 further comprising a sensory stimulation module operatively connectable to the control system and to the patient to provide sensory feedback thereto.

3. The device of claim 2 wherein the sensory stimulation module includes a tongue stimulator operatively connectable to a tongue of the patient.

4. The device of claim 1 wherein the control system includes a central processing unit interconnecting the sensor system and the functional stimulation component, the central processing unit generating the control signals.

5. The device of claim 1 wherein the sensor system includes an electroencephalography sensor.

6. The device of claim 1 wherein:
the control system includes a central processing unit;
the sensor system includes a plurality of sensors;
each channel of the functional stimulation component includes a muscle stimulator connectable to one of the different muscle sites of the limb; and
the central processing unit is operatively connected to each channel of the functional stimulation component; and
wherein the device further comprises:
a multichannel amplifier interconnecting each of the plurality of sensors to the central processing unit.

7. The device of claim 6 further comprising a sensory stimulation module operatively connected to the central processing unit and operatively connectable to the patient to provide sensory feedback thereto.

8. The device of claim 7 wherein the sensory stimulation module includes a tongue stimulator operatively connectable to a tongue of the patient.

9. The device of claim 1 wherein the predetermined set of patient parameters include a location of the sensory motor disability and a time period since the onset of the sensory motor disability.

10. A closed loop, neural activity triggered rehabilitation device for facilitating recovery of a patient from the effects of a sensory motor disability, the patient including a brain and a limb having a plurality of muscle sites, the device comprising:
a sensor system positionable adjacent the brain at a predetermined location, the sensor system configured to detect real-time neural signals at the predetermined location corresponding to an area of the brain used by the patient to move the limb contemporaneously with volitional commands of the brain by the patient;
a control system operatively connected to the sensor system for receiving the real-time neural signals from the sensor system, the control system generating a plurality of unique, synchronized control signals which are based on the real-time neural signals and a predetermined set of patient parameters, without utilizing any neural signals of the patient obtained previous to and non-contemporaneously with the real-time neural signals, wherein the predetermined set of patient parameters are independent of real time patient feedback including the location of an injury to the patient, a motor deficit suffered by the patient as a result of the injury and time that has passed since the injury;
a functional stimulation component operatively connectable to the control system and including a plurality of channels, each channel of the plurality of channels operatively connectable to a different muscle site of the limb to stimulate a corresponding different muscle site in response to the corresponding one of the plurality of unique, synchronized control signals received from the control system.

11. The device of claim 10 further comprising a sensory stimulation module operatively connectable to the patient to provide sensory feedback thereto.

12. The device of claim 11 wherein the sensory stimulation module includes a tongue stimulator operatively connectable to a tongue of the patient.

13. The device of claim 10 wherein the control system includes a central processing unit interconnecting a plurality of sensors of the sensor system and the plurality of channels.

14. The device of claim 13 wherein the plurality of sensors are electroencephalography sensors.

15. The device of claim 10 wherein:
the sensor system includes a plurality of sensors;
the control system includes a central processing unit opera connected to the plurality of channels; and
the device further comprises a multichannel amplifier interconnecting each of the plurality of sensors to the central processing unit.

16. The device of claim 15 further comprising a sensory stimulation module operatively connected to the central processing unit and operatively connectable to the patient to provide sensory feedback thereto.

17. The device of claim 16 wherein the sensory stimulation module includes a tongue stimulator operatively connectable to a tongue of the patient.

* * * * *